United States Patent [19]

Wierenga

[11] 4,140,850
[45] Feb. 20, 1979

[54] 2,2'-ANHYDROTRIAZINE NUCLEOSIDES AND PROCESS FOR PREPARING THE SAME

[75] Inventor: Wendell Wierenga, Kalamazoo, Mich.

[73] Assignee: The Upjohn Company, Kalamazoo, Mich.

[21] Appl. No.: 828,797

[22] Filed: Aug. 29, 1977

[51] Int. Cl.$^2$ ........................................... C07H 17/00
[52] U.S. Cl. .................................... 536/23; 424/180
[58] Field of Search .......................................... 536/23

[56] References Cited

U.S. PATENT DOCUMENTS

| 3,658,788 | 4/1972 | Orgel et al. | 536/23 |
| 3,907,779 | 9/1975 | DeBoer | 536/23 |

OTHER PUBLICATIONS

Wierenga, W. and Woltersom, A., J. Org. Chem., 43,529 (1978).
Wierenga, W. and Woltersom, A., 172nd National Meeting of American Chemical Society 1976, Asbtracts No. CHRB 44.

Primary Examiner—Johnnie R. Brown
Assistant Examiner—Blondel Hazel
Attorney, Agent, or Firm—William G. Jameson

[57] ABSTRACT

Novel anhydroarabinofuranosyldihydrotriazine nucleosides and process for preparing the same. The compounds of formula I are useful as immunosuppressive agents in humans and are also active in vitro against various susceptible Herpes Viruses.

16 Claims, No Drawings

2,2'-ANHYDROTRIAZINE NUCLEOSIDES AND PROCESS FOR PREPARING THE SAME

BACKGROUND OF THE INVENTION

Winkley and Robins, J. Org. Chem., 35, pp. 491–496 (1970) describes the preparation of β-D-ribofuranosyl-1,3,5-triazine-5-N-methyl-2,4,6-trione from the trimethylsilyl derivative of 1-methylcyanuric acid and 2,3,5-tri-O-benzoyl-D-ribofuranosyl bromide. NMR studies of β-D-ribofuranosyl-1,3,5-triazine-5-N-methyl-2,4,6-trione or β-D-ribofuranosyl-1,3,5-triazine-2,4,6-trione are reported in J. Am. Chem. Soc., 93, 3469, 4334 (1971) and J. Phys. Chem., 74, 2684 (1970).

The utilization of tert-butyldimethylsilyl protecting groups in nucleoside chemistry was disclosed by K. K. Ogilvie, et. al., Tet. Letters, 2681 (1974).

R. A. Sanchez and L. E. Orgel, J. Mol. Biol. 47, 531 (1970) describe the preparation of cytosine arabinoside by reaction of aminoarabinofuranooxazoline with cyanoacetylene in N,N-dimethylacetamide and subsequent aqueous hydrolysis. See also U.S. Pat. 3,658,788.

E. A. Falco et al., J. Org. Chem., 35, 2326 (1970) describes the preparation of 5,2'-anhydrouridine from various nucleosides.

SUMMARY OF THE INVENTION

This description pertains to new organic chemical compounds and a process for preparing the same. The description is more particularly directed to new arabinofuranosyldihydrotriazine nucleosides prepared from 2-amino-β-D-arabinofurano-[1',2':4,5]-2-oxazoline. The arabinofuranosyldihydrotriazine and anhydroarabinofuranosyldihydrotriazine nucleosides of the subject description can be utilized as immunosuppressant agents and are formulated with pharmaceutical carriers for oral or parenteral means of administration.

DETAILED DESCRIPTION OF THE INVENTION

The novel 2,2'-anhydronucleosides of the subject invention are represented by formula I

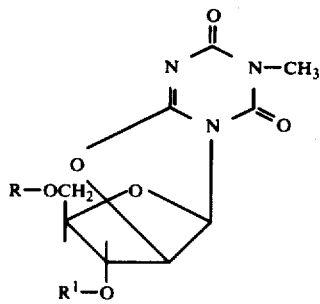

where R and $R^1$ can be the same or different, and are selected from the group consisting of hydrogen; adamantoyl, substituted with zero through one substituent selected from the group consisting of —$CH_2CO_2H$ and —$CH_2CO_2CH_3$; or the radical

XC— wherein X is selected from the group consisting of phenyl, substituted with zero through three substituents, which can be the same or different and are selected from the group consisting of halogen, alkyl of one through six carbon atoms, dialkylamino where the alkyl groups contain one through six carbon atoms and can be the same or different, trifluoromethyl, alkoxy where the alkyl group contains one through six carbon atoms, cyano, carboxy, carbomethoxy, and carbethoxy; α- or β-naphthyl; alkyl of one through 12 carbon atoms, substituted with zero through one substituents selected from the group consisting of phenyl, cyano, nitro, halogen and carboxy; and alkoxy where the alkyl group contains one through 12 carbon atoms, substituted with zero through one substituents selected from the group consisting of phenyl, cyano, nitro, halogen and carboxy; provided that when one member (R or $R^1$) is not hydrogen, the other member is the same or hydrogen.

The novel arabinofuranosyldihydrotriazine nucleosides of the subject invention are represented by formula II

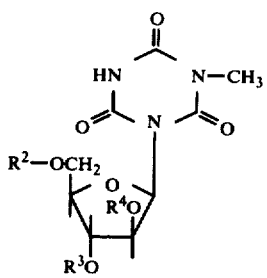

wherein $R^2$, $R^3$ and $R^4$ can be the same or different; and are selected from the group consisting of hydrogen; adamantoyl, substituted with zero through one substituents selected from the group consisting of $CH_2CO_2H$ and $CH_2CO_2CH_3$; of the radical

XC— wherein X is selected from the group consisting of phenyl, substituted with zero through three substituents, which can be the same or different and are selected from the group consisting of halogen, alkyl of one through six carbon atoms, dialkylamino where the alkyl groups contain one through six carbon atoms and can be the same or different, trifluoromethyl, alkoxy where the alkyl group contains one through six carbon atoms, cyano, carboxy, carbomethoxy and carbethoxy; α- or β-naphthyl; alkyl of one through 12 carbon atoms, substituted with zero through one substituents selected from the group consisting of phenyl, cyano, nitro, halogen and carboxy; and alkoxy where the alkyl group contains one through 12 carbon atoms, substituted with zero through one substituents selected from the group consisting of phenyl, cyano, nitro, halogen, and carboxy; provided that two or more of the members ($R^2$, $R^3$ and $R^4$) are the same and when a first member is not hydrogen, the other members are the same as the first member or hydrogen and further provided that when $R^3$ is hydrogen, one of $R^2$ and $R^4$ must also be hydrogen and still further provided that when $R^3$ is not hydrogen, $R^2$ and $R^4$ cannot both be hydrogen.

The purpose of the above provisos are to exclude mixed esters, 3'-mono-esters and 2',5'-diesters of formula II from the scope of the subject application.

The novel process of this invention is illustratively represented by the following reaction sequence:

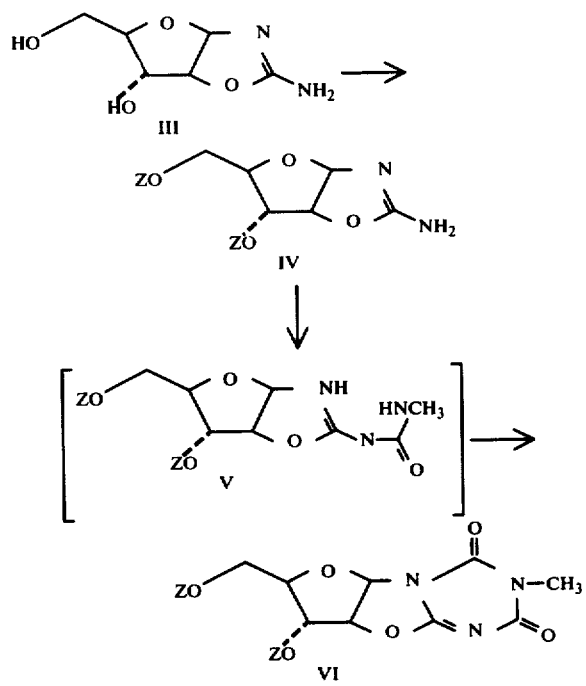

wherein Z is tert-butyldimethylsilyl. The brackets around the formula of the second intermediate (V) indicate that the structure of the intermediate is hypothetical and that it could possibly exist as the isomer:

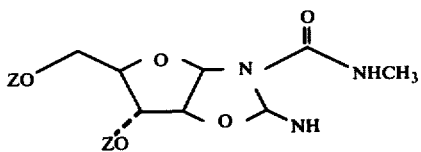

The broken line (--) joining ZO and HO to the body of the molecule indicates that ZO and HO are in the α (alpha) configuration.

A group of compounds within the scope of formula I are those wherein $R^1$ is hydrogen.

Another group of compounds within the scope of formula I are those wherein R is hydrogen.

Still another group of compounds within the scope of formula I are those wherein $R^1$ is hydrogen and R is the radical

XC— wherein X is selected from the group consisting of lower alkyl of one through four carbon atoms, phenyl, 2-carboxyethyl ($CH_2CH_2CO_2H$).

Another group of compounds within the scope of formula I are those wherein R' is hydrogen and R is the radical

XC— wherein X is alkoxy where the alkyl group contains one through six carbon atoms.

The preferred compound of formula I is β-D-arabinofuran[1',2':4,5]-oxazolo-1,3,5-triazine-5-N-methyl-4,6-dione.

A group of compounds within the scope of formula II are those wherein $R^3$ and $R^4$ are hydrogen.

Another group of compounds within the scope of formula II are those wherein $R^2$ and $R^3$ is hydrogen.

Another group of compounds within the scope of formula II are those wherein $R^4$ is hydrogen.

A group of compounds within the scope of formula II are those wherein $R^2$ is hydrogen.

Still another group of compounds within the scope of formula II are those wherein $R^3$ and $R^4$ are hydrogen and $R^2$ is the radical

XC— wherein X is selected from the group consisting of lower alkyl of one through four carbon atoms, phenyl and 2-carboxyethyl ($CH_2CH_2CO_2H$).

Another group of compounds within the scope of formula II are those wherein $R^3$ and $R^4$ are hydrogen and $R^2$ is the radical

XC— wherein X is alkoxy where the alkyl group contains one through six carbon atoms.

The preferred compound of formula II is β-D-arabinofuranosyl-1,3,5-triazine-5-N-methyl-2,4,6-trione.

The definitions and explanations below are for the terms as used throughout the entire patent application including the specification and claims.

All temperatures are in degrees centigrade.

DMF refers to dimethylformamide.

THF refers to tetrahydrofuran.

TLC refers to thin layer chromatography.

Glpc refers to gas-liquid phase chromatography.

GC-MS refers to gas chromatography-mass spectrometry.

Amberlite ® IR 120($H^+$) refers to a sulfonic acid ion exchange resin, marketed by Mallinckrodt.

UCW ® refers to a brand of liquid phase support for glpc.

The term "halogen" as used throughout the specification and claims includes fluoro, chloro, bromo, and iodo. The term dialkylamino where the alkyl groups contain one through six carbon atoms includes, for example, dimethylamino, diethylamino and methylethylamino.

The term "alkyl" is employed in its usual sense as meaning alkyl such as methyl, ethyl, propyl, butyl, pentyl, hexyl, octyl, dodecyl and isomers thereof.

The term "adamantoyl" is employed in its usual sense as meaning 1-carbonyl adamantane, i.e. 1-adamantylcarbonyl.

The term "adamantoyl, substituted with zero through one substituents selected from the group consisting of $CH_2COOH$ and $CH_2COOCH_3$," means 1-adamantylcarbonyl substituted at the 3-position with carboxymethyl ($CH_2COOH$) or (methoxycarbonyl)methyl.

The compounds of formula I are useful as immunosuppressive agents in humans and also are active in vitro against various susceptible DNA viruses, for example susceptible Herpes viruses including the Herpes simplex type 1 virus and thus can be used to inhibit the growth of susceptible DNA viruses in tissue culture medium at a concentration of from about 20 to about 200 mcg./ml. (micrograms of compound per ml. of tissue culture medium).

The compounds of formula II are useful as immunosuppressive agents in humans.

The compounds of formula I or II, and appropriate pharmaceutical preparations containing effective levels of the compound can be used as immunosuppressive agents to alleviate the graft rejection process in humans, and hence can be used in rejection therapy associated with skin grafting or organ transplantation. In addition, the compounds of formula I or II can be used as immunosuppressive agents for the relief of rheumatoid arthritis and other progressive antigenic insult situations.

An effective quantity of the compound is employed in treatment. The dosage of the compound for treatment depends on the route of administration and the potency of the particular compound. In general, a dose of from about 50 mg./kg./day to about 400 mg./kg./day embraces the effective range and can be administered orally or parenterally for the prevention and/or alleviation of the tissue rejection process. It is desirable to administer the dose in increments throughout the day in order that elevated blood levels of the compound can be maintained. The dosage schedule is started about 2 days to 7 days prior to antigenic insult and continued for a period of time, not less than 15 days following insult.

Progressive situations such as rheumatoid arthritis can be controlled by long-term oral or parenteral administration, in divided doses, of from 50 mg./kg./day to about 500 mg./kg./day.

Avoidance of systemic toxicities such as hepatoxicity, diarrhea and abdominal pain by the use of the minimum effective dose is desirable.

Following is an illustrative list of compounds of formula I which can be prepared by acylating β-D-arabinofuran[1',2':4,5]-oxazolo-1,3,5-triazin-5-N-methyl-4,6-dione with the appropriate acid halide in the manner described herein.

TABLE 1

1. 3',5'-bis(O-acetyl)-β-D-arabinofuran-[1',2':4,5]-oxazolo-1,3,5-triazin-5-N-methyl-4,6-dione.
2. 5'-O-acetyl-β-D-arabinofuran[1',2':4,5]oxazolo-1,3,5-triazin-5-N-methyl-4,6-dione.
3. 3'-O-acetyl-β-D-arabinofuran[1',2':4,5]-oxazolo-1,3,5-triazin-5-N-methyl-4,6-dione.
4. 3',5'-bis(O-benzoyl)-β-D-arabinofuran[1',2':4,5]-oxazolo-1,3,5-triazin-5-N-methyl-4,6-dione.
5. 5'-O-benzoyl-β-D-arabinofuran[1',2':4,5]oxazolo-1,3,5-triazin-5-N-methyl-4,6-dione.
6. 3'-O-benzoyl-β-D-arabinofuran[1',2':4,5]-oxazolo-1,3,5-triazin-5-N-methyl-4,6-dione.
7. 3',5'-bis(O-β-chloropivaloyl)-β-D-arabinofuran[1',2':4,5]-oxazolo-1,3,5-triazin-5-N-methyl-4,6-dione.
8. 5'-O-β-chloropivaloyl-β-D-arabinofuran-[1',2':4,5]-oxazolo-1,3,5-triazin-5-N-methyl-4,6-dione.
9. 3'-O-β-chloropivaloyl-β-D-arabinofuran[1',2':4,5]-oxazolo-1,3,5-triazin-5-N-methyl-4,6-dione.
10. 3',5'-bis(O-pivaloyl)-β-D-arabinofuran[1',2':4,5]-oxazolo-1,3,5-triazin-5-N-methyl-4,6-dione.
11. 5'-O-pivaloyl-β-D-arabinofuran[1',2':4,5]-oxazolo-1,3,5-triazine-5-N-methyl-4,6-dione.
12. 3'-O-pivaloyl-β-D-arabinofuran[1',2':4,5]-oxazolo-1,3,5-triazin-5-N-methyl-4,6-dione.
13. 3',5'-bis(o-isobutyryl-β-D-arabinofuran[1',2':4,5]-oxazolo-1,3,5-triazin-5-N-methyl-4,6-dione.
14. 5'-O-isobutyryl-β-D-arabinofuran[1',2':4,5]-oxazolo-1,3,5-triazin-5-N-methyl-4,6-dione.
15. 3',5'-bis(O-p-nitrobenzoyl)-β-D-arabinofuran[1',2':4,5]-oxazolo-1,3,5-triazin-5-N-methyl-4,6-dione.
16. 5'-O-p-nitrobenzoyl-β-D-arabinofuran[1',2':4,5]-oxazolo-1,3,5-triazin-5-N-methyl-4,6-dione.
17. 3'-O-p-nitrobenzoyl-β-D-arabinofuran[1',2':4,5]-oxazolo-1,3,5-triazin-5-N-methyl-4,6-dione.
18. 3',5'-bis(O-o-toluoyl)-β-D-arabinofuran[1',2':4,5]-oxazolo-1,3,5-triazin-5-N-methyl-4,6-dione.
19. 5'-O-o-toluoyl-β-D-arabinofuran[1',2':4,5]-oxazolo-1,3,5-triazin-5-N-methyl-4,6-dione.
20. 3'-O-o-toluoyl-β-D-arabinofuran[1',2':4,5]-oxazolo-1,3,5-triazin-5-N-methyl-4,6-dione.
21. 3',5'-bis(O-2,6-dimethylbenzoyl)-β-D-arabinofuran[1',2':4,5]-oxazolo-1,3,5-triazin-5-N-methyl-4,6-dione.
22. 5'-O-2,6-dimethylbenzoyl-β-D-arabinofuran[1',2':4,5]-oxazolo-1,3,5-triazin-5-N-methyl-4,6-dione.
23. 3'-O-2,6-dimethylbenzoyl-β-D-arabinofuran[1',2':4,5]-oxazolo-1,3,5-triazin-5-N-methyl-4,6-dione.
24. 3',5'-bis(O-2,4,6-trimethylbenzoyl)-β-D-arabinofuran[1',2':4,5]-oxazolo-1,3,5-triazin-5-N-methyl-4,6-dione.
25. 5'-O-2,4,6-trimethylbenzoyl-β-D-arabinofuran[1',2':4,5]-oxazolo-1,3,5-triazin-5-N-methyl-4,6-dione.
26. 3'-O-2,4,6-trimethylbenzoyl-β-D-arabinofuran[1',2':4,5]-oxazolo-1,3,5-triazin-5-N-methyl-4,6-dione.
27. 3',5'-bis(O-p-anisoyl)-β-D-arabinofuran[1',2':4,5]-oxazolo-1,3,5-triazin-5-N-methyl-4,6-dione.
28. 5'-O-p-anisoyl-β-D-arabinofuran[1',2':4,5]-oxazolo-1,3,5-triazin-5-N-methyl-4,6-dione.
29. 3'-O-p-anisoyl-β-D-arabinofuran[1',2':4,5]-oxazolo-1,3,5-triazin-5-N-methyl-4,6-dione.
30. 3',5'-bis(O-3,4,5-trimethoxybenzoyl)-β-D-arabinofuran[1',2':4,5]-oxazolo-1,3,5-triazin-5-N-methyl-4,6-dione.
31. 5'-O-3,4,5-trimethoxybenzoyl-β-D-arabinofuran[1',2':4,5]-oxazolo-1,3,5-triazin-5-N-methyl-4,6-dione.
32. 3'-O-3,4,5-trimethoxybenzoyl-β-D-arabinofuran1',2':4,5]-oxazolo-1,3,5-triazin-5-N-methyl-4,6-dione.
33. 3',5'-bis(O-p-toluoyl)-β-D-arabinofuran[1',2':4,5]-oxazolo-1,3,5-triazin-5-N-methyl-4,6-dione.
34. 5'-O-p-toluoyl-β-D-arabinofuran[1',2':4,5]-oxazolo-1,3,5-triazin-5-N-methyl-4,6-dione.
35. 3'-O-tolyl-β-D-arabionfuran[1',2':4,5]-oxazolo-1,3,5-triazin-5-N-methyl-4,6-dione.
36. 3',5'-bis(O-1-naphthoyl)-β-D-arabinofuran[1',2':4,5]-oxazolo-1,3,5-triazin-5-N-methyl-4,6-dione.
37. 5'-O-(1-naphthoyl)-β-D-arabinofuran[1',2':4,5]-oxazolo-1,3,5-triazin-5-N-methyl-4,6-dione.
38. 3'-O-(1-naphthoyl)-β-D-arabinofuran[1',2':4,5]-oxazolo-1,3,5-triazin-5-N-methyl-4,6-dione.

39. 3',5'-bis(O-adamantoyl)-β-D-arabinofuran[1',2':4,5]-oxazolo-1,3,5-triazin-5-N-methyl-4,6-dione.
40. 5'-O-adamantoyl-β-D-arabinofuran[1',2':4,5]-oxazolo-1,3,5-triazin-5-N-methyl-4,6-dione.
41. 3'-O-adamantoyl-β-D-arabinofuran[1',2':4,5]-oxazolo-1,3,5-triazin-5-N-methyl-4,6-dione.
42. 3',5'-bis(O-carbomethoxy)-β-D-arabinofuran[1',2':4,5]-oxazolo-1,3,5-triazin-5-N-methyl-4,6-dione.
43. 5'-O-carbomethoxy-β-D-arabinofuran[1',2':4,5]-oxazolo-1,3,5-triazin-5-N-methyl-4,6-dione.
44. 3'-O-carbomethoxy-β-D-arabinofuran1',2':4,5]-oxazolo-1,3,5-triazin-5-N-methyl-4,6-dione.
45. 5'-O-3-(carboxymethyl)adamantoyl-β-D-arabinofuran[1',2':4,5]-oxazolo-1,3,5-triazin-5-N-methyl-4,6-dione.
46. 5'-O-3-[(methoxycarbonyl)methyl]-adamantoyl-β-D-arabinofuran[1',2':4,5]-oxazolo-1,3,5-triazin-5-N-methyl-4,6-dione.

Following is an illustrative list of compounds of formula II which can be prepared by acylating β-D-arabinofuranosyl-1,3,5-triazine-5-N-methyl-2,4,6-trione with the appropriate acid halide in the manner described herein.

TABLE II 1. 2',3',5'-tri-O-acetyl-β-D-arabinofuranosyl-1,3,5-triazine-5-N-methyl-2,4,6-trione.
2. 5'-O-acetyl-β-D-arabinofuransoyl-1,3,5-triazine-5-N-methyl-2,4,6-trione.
3. 2',3'-bis-O-acetyl-β-D-arabinofuranosyl-1,3,5-triazine-5-N-methyl-2,4,6-trione.
4. 3',5'-bis-O-acetyl-β-D-arabinofuranosyl-1,3,5-triazine-5-N-methyl-2,4,6-trione.
5. 2'-O-acetyl-β-D-arabinofuranosyl-1,3,5-triazine-5-N-methyl-2,4,6-trione.
6. 3',5'-bis(O-β-chloropivaloyl)-β-D-arabinofuranosyl-1,3,5-triazine-5-N-methyl-2,4,6-trione.
7. 5'-O-β-chloropivaloyl-β-D-arabinofuranosyl-1,3,5-triazine-5-N-methyl-2,4,6-trione.
8. 2'-O-β-chloropivaloyl-β-D-arabinofuranosyl-1,3,5-triazine-5-N-methyl-2,3,6-trione.
9. 3',5'-bis-(O-pivaloyl)-β-D-arabinofuranosyl-1,3,5-triazine-5-N-methyl-2,4,6-trione.
10. 5'-O-pivaloyl-β-D-arabinofuranosyl-1,3,5-triazine-5-N-methyl-2,4,6-trione.
11. 2'-O-pivaloyl-β-D-arabinofuranosyl-1,3,5-triazine-5-N-methyl-2,4,6-trione.
12. 3',5'-bis(o-isobutyryl-β-D-arabinofuranosyl-1,3,5-triazine-5-N-methyl-2,4,6-trione.
13. 5'-O-isobutyryl-β-D-arabinofuranosyl-1,3,5-triazine-5-N-methyl-2,4,6-trione.
14. 3',5'-bis(O-p-nitrobenzoyl)-β-D-arabinofuranosyl-1,3,5-triazine-5-N-methyl-2,4,6-trione.
15. 5'-O-p-nitrobenzoyl-β-D-arabinofuranosyl-1,3,5-triazine-5-N-methyl-2,4,6-trione.
16. 2'-O-p-nitrobenzoyl-β-D-arabinofuranosyl-1,3,5-triazine-5-N-methyl-2,4,6-trione.
17. 3',5'-bis(O-o-toluoyl)-β-D-arabinofuranosyl-1,3,5-triazine-5-N-methyl-2,4,6-trione.
18. 5'-O-o-toluoyl-β-D-arabinofuranosyl-1,3,5-triazine-5-N-methyl-2,4,6-trione.
19. 2'-O-o-toluoyl-β-D-arabinofuranosyl-1,3,5-triazine-5-N-methyl-2,4,6-trione.
20. 3',5'-bis(O-2,6-dimethylbenzoyl)-β-D-arabinofuranosyl-1,3,5-triazine-5-N-methyl-2,4,6-trione.
21. 5'-O-2,6-dimethylbenzoyl-β-D-arabinofuranosyl-1,3,5-triazine-5-N-methyl-2,4,6-trione.
22. 2'-O-2,6-dimethylbenzoyl-β-D-arabinofuranosyl-1,3,5-triazine-5-N-methyl-2,4,6-trione.
23. 3',5'-bis(O-2,4,6-trimethylbenzoyl)-β-D-arabinofuranosyl-1,3,5-triazine-5-N-methyl-2,4,6-trione.
24. 5'-O-2,4,6-trimethylbenzoyl-β-D-arabinofuranosyl-1,3,5-triazine-5-N-methyl-2,4,6-trione.
25. 3'-O-2,4,6-trimethylbenzoyl-β-D-arabinofuranosyl-1,3,5-triazine-5-N-methyl-2,4,6-trione.
26. 3',5'-bis(O-p-anisoyl)-β-D-arabinofuranosyl-1,3,5-triazine-5-N-methyl-2,4,6-trione.
27. 5'-O-p-anisoyl-β-D-arabinofuranosyl-1,3,5-triazine-5-N-methyl-2,4,6-trione.
28. 2'-O-p-anisoyl-β-D-arabinofuranosyl-1,3,5-triazine-5-N-methyl-2,4,6-trione.
29. 3',5'-bis(O-3,4,5-trimethoxybenzoyl)-β-D-arabinofuranosyl-1,3,5-triazine-5-N-methyl-2,4,6-trione.
30. 5'-O-3,4,5-trimethoxybenzoyl-β-D-arabinofuranosyl-1,3,5-triazine-5-N-methyl-2,4,6-trione.
31. 3'-O-3,4,5-trimethoxybenzoyl-β-D-arabinofuranosyl-1,3,5-triazine-5-N-methyl-2,4,6-trione.
32. 3',5'-bis(O-p-toluoyl)-β-D-arabinofuranosyl-1,3,5-triazine-5-N-methyl-2,4,6-trione.
33. 2',3',5'-tri-P-benzoyl-β-D-arabinofuranosyl-1,3,5-triazine-5-N-methyl-2,4,6-trione.
34. 5'-O-benzoyl-β-D-arabinofuranosyl-1,3,5-triazine-5-N-methyl-2,4,6-trione.
35. 2',3',5'-tri-O-carbomethoxy-β-D-arabinofuranosyl-1,3,5-triazine-5-N-methyl-2,4,6-trione.
36. 5'-O-carbomethoxy-β-D-arabinofuranosyl-1,3,5-triazine-5-N-methyl-2,4,6-trione.
37. 5'-O-adamantoyl-β-D-arabinofuranosyl-1,3,5-triazine-5-N-methyl-2,4,6-trione.
38. 2',3',5'-tri-O-(2-naphthoyl)-β-D-arabinofuranosyl-1,3,5-triazine-5-N-methyl-2,4,5-trione.
39. 5'-O-(2-naphthoyl)-β-D-arabinofuranosyl-1,3,5-triazine-5-N-methyl-2,4,6-trione.

The starting 2-amino-β-D-arabinofurano[1',2':4,5]-2-oxazoline of formula III, utilized in the process of the present invention, can be prepared utilizing the process of Sanchez et al., J. Mol. Biol., 47, 531–543 (1970) which involves reacting D-arabinose and cyanamide.

In carrying out the process of this invention, the aminooxazoline moiety (III) is subjected to the following reaction steps:

The aminooxazoline (III) is suspended in a suitable inert organic solvent under nitrogen at a relatively low temperature, such as from about 0° to about 30° C. Suitable inert organic solvents which can be used include, for example, THF, hexamethylphosphoric triamide, and N,N-dimethylformamide (DMF). DMF is preferred. The solution thus obtained is treated with tert-butyldimethylsilyl chloride at a relatively low temperature, such as from about 0° to about 30° C. The time required for silylation of the aminooxazoline (III) to obtain the corresponding 2-amino-3,5-bis(o-tert-butyldimethylsilyl)-β-D-arabinofuran[1',2':4,5]-2-oxazoline of formula IV is dependent in part on the temperature at which the reaction is carried out, a temperature between about 0° to about 20° C. can be employed for a period of from about 2 to 3 hours for completion of the reaction. The compounds of formula IV thus obtained can be recovered from the reaction mixture and purified by conventional methods, for example by recrystallization from hexane.

The compound of formula IV thus obtained is then ionized with a suitable base such as n-butyl lithium, potassium t-butoxide, or sodium hydride in a suitable inert organic solvent such as DMF under nitrogen. Sodium hydride is preferred. The reaction is carried out within a broad temperature range, for example from about 0° C. to about 30° C. for a period of time of from about 15 to about 60 minutes, however, temperatures within about 25° C. are preferred. Advantageously, the reaction mixture is cooled to a relatively low temperature, such as from about 0° to about 5° C. and methyl isocyanate is then added slowly and the reaction mixture is stirred for a period of time of from about 30 to about 60 minutes. The compound of formula V thus obtained is recovered and purified by conventional methods or used directly in the next step without recovery from the reaction medium.

The compound of formula V thus obtained is then subject to ring-closure with 1,1'-carbonyl diimidazole or other suitable carbonyl equivalent groups such as phosgene or diethyl carbonate to obtain the compound of formula VI. The ring-closure is carried out within a temperature range of from about 0° to about 30° C., for a period of time of from about 1 to about 3 hours. The product (VI), thus obtained, is recovered from the reaction mixture and purified by conventional methods, for example, silica gel chromatography.

The removal of the tert-butyldimethylsilyl protecting groups on the product 3',5'-bis(O-tert-butyldimethylsilyl)-β-D-arabinofuran[1',2':4,5]-oxazolo-1,3,5-triazin-5-N-methyl-4,6-dione can be readily effected under anhydrous conditions by conventional methods utilizing tetra-n-butyl ammonium fluoride in THF prepared utilizing the procedure of Pless, J. Org. Chem., 39, 2645 (1974), and after acetylation the compound 3',5'-bis(O-acetyl)-β-D-arabinofuran[1',2':4,5]-oxazolo-1,3,5-triazin-5-N-methyl-4,6-dione is recovered. If desired, the compound β-D-arabinofuran[1',2':4,5]-oxazolo-1,3,5-triazin-5-N-methyl-4,6-dione is obtain following mild ester hydrolysis of the compound 3',5'-bis(O-acetyl)-β-D-arabinofuran[1',2':4,5]-oxazolo-1,3,5-triazin-5-N-methyl-4,6-dione by conventional methods (methanolic ammonia). Upon stronger basic hydrolysis, the compound β-D-arabinofuranosyl-1,3,5-triazine-5-N-methyl-2,4,6-trione can be obtained.

The removal of the tert-butyldimethylsilyl protecting groups on the product 3',5'-bis(O-tert-butyldimethylsilyl)-β-D-arabinofuran[1',2':4,5]-oxazolo-1,3,5-triazine-5-N-methyl-4,6-dione under non-anhydrous conditions utilizing tetra-n-butyl ammonium fluoride in THF can be effected and after acetylation the compound 2',3',5'-tri-O-acetyl-β-D-arabinofuranosyl-1,3,5-triazine-5-N-methyl-2,4,6-trione recovered. If desired, the compound β-D-arabinofuranosyl-1,3,5-triazine-5-N-methyl-2,4,6-trione can also be obtained following ester hydrolysis (methanolic ammonia) of 2',3',5'-tri-O-acetyl-β-D-arabinofuranosyl-1,3,5-triazine-5-N-methyl-2,4,6-trione.

The free nucleosides of the invention, compounds according to formula I and II wherein R, R¹, R², R³ and R⁴ are hydrogen, can be acylated by standard procedures utilizing an acid halide or anhydride of an appropriate carboxylic acid including, for example, acetic anhydride, acetyl chloride, benzoyl chloride, succinic anhydride, and methyl chloro formate.

Various acylates of the free nucleosides of the invention can be made, and these acylates are useful to upgrade the free nucleosides.

The 5'-mono-esters can be formed by standard procedure using a minimum amount of acylating agents.

The 3'-mono-esters of formula I can be formed by tritylating the free nucleoside to give the 5'-trityl derivative, acylating with the acid halide or anhydride of an appropriate carboxylic acid such as those disclosed in U.S. Pat. No. 3,426,012, Columns 5 and 6, to give the 3'-mono-ester 5'-trityl derivative, which then can be converted to the 3'-mono-ester by removal of the trityl group.

The 2'-mono-esters of formula II can be formed by reacting the free nucleoside with trichloroethyl chloroformate (Cl₃CCH₂O₂Cl) to give the 3',5'-bis-protected derivatives, acylating with the desired acid chloride and then removing the 3',5'-protecting groups using zinc in acetic acid to give the 2'-mono-ester.

The 2',3'-diesters of formula II can be formed by tritylating the free nucleoside to give the 5'-trityl derivative, acylating with the acid halide or anhydride of an appropriate carboxylic acid to give the 2',3'-diester 5'-trityl derivative, which then can be converted to the 2',3'-mono-ester by removal of the trityl group.

The 3',5'-diesters of formula II can be formed by reaction of the nucleoside in pyridine with the desired acid chloride as disclosed in J. A. Montgomery and H. J. Thomas, J. Med. Chem., 15, 116 (1972).

The 3',5'-diesters of formula I and 2',3',5'-triesters of formula II can be formed by fully acylating the hydroxyl groups of the free nucleosides using standard procedures.

Alternatively, the compound β-D-arabinofuran[1',2':4,5]-oxazolo-1,3,5-triazin-5-N-methyl-4,6-dione can be prepared from 3',5'-bis(O-trimethylsilyl)-β-D-arabinofuran[1',2':4,5]-oxazolo-1,3,5-triazin-5-N-methyl-4,6-dione by the following reaction sequence:

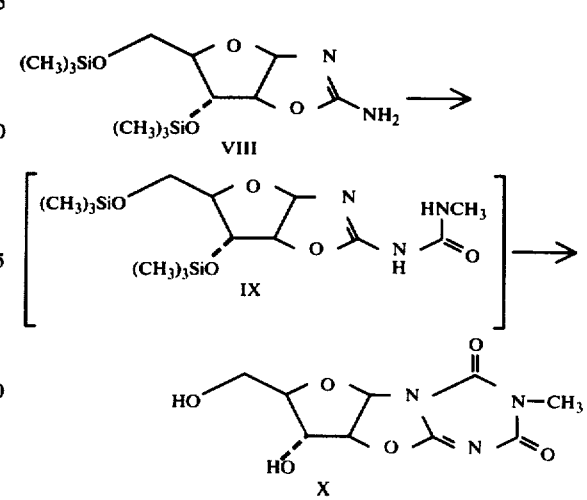

The brackets around the formula of the intermediate IX indicate that the structure is hypothetical and that it could possibly exist as the isomer (XI):

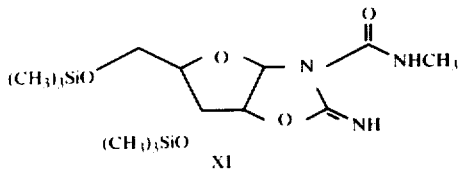

XI

The broken line (--) joining HO and (CH₃)₃SiO to the body of the molecule indicates that the substituents are in the α (alpha) configuration.

The starting 3',5'-bis(O-trimethylsilyl)-β-D-arabinofuran[1',2':4,5]-oxazolo-1,3,5-triazin-5-N-methyl-4,6-dione of formula VIII can be prepared utilizing the process of Hessler, J. Org. Chem., 41, 1828 (1976).

In carrying out the alternate process of this invention, the starting material (VIII) is subjected to the following reaction steps:

The starting material (VIII) is suspended in a suitable inert organic solvent under nitrogen at a low temperature, such as from about −30° C. to about −80° C., and ionized with n-butyl lithium or other alkyl or aryl lithium. Suitable inert organic solvents which can be used for the alternate process include, for example, THF, dimethoxyethane, dioxane and diglyme ®. THF is preferred. DMF is unsuitable.

After ionization, the reaction mixture is allowed to warm to about −10° to about 0° C. and methyl isocyanate is added slowly with stirring. After a period of time of about 5 min., ring-closure is carried out utilizing 1,1'-carbonyl diimidazole or phosgene. The 1,1'-carbonyl diimidazole or phosgene is added to the reaction and the reaction mixture is stirred until ring closure is complete, advantageously the temperature is increased at a moderate rate to about 30° C. The reaction solution is taken up in a polar organic solvent such as ethyl acetate, chloroform or diethylether and the organic phase(s) concentrated. The resulting residue is subjected to mild aqueous acid hydrolysis and the product (X) is recovered and purified by conventional methods, for example, silica gel chromatography.

The invention can be more fully understood by the following examples which are intended not to limit but merely to exemplify the nature of the invention.

EXAMPLE 1

2-Amino-3',5'-bis(o-tert-butyldimethylsilyl)-β-D-arabinofuran[1',2':4,5]-2-oxazoline To 3.48 g. (0.02 mole) of 2-amino-β-D-arabinofuran-[1',2':4,5]-2-oxazoline in 50 ml. of dry DMF (distilled from CaH₂ and stored over activated 4A molecular seive) under N₂ in an ice bath is added 3.40 g. (0.05 mole) of imidazole followed by 7.5 g. (0.05 mole) of tert-butyldimethylsilyl chloride. After 15 minutes the now homogeneous solution is allowed to come to room temperature and stirred for another two hours. The solution is poured into a stirred, cold 2% sodium carbonate solution (3000 ml.), filtered after ten minutes, washed with 50 ml. cold water and then allowed to partially dry at room temperature for several hours. The off-white solid is azeotroped once with benzene and then dissolved in hexane (250 ml.) with heating, allowed to cool, crystallize, and then filtered and dried at room temperature (Note: product sublimes even at 25 mm/25°). Final recovery from mother liquor yields a total of 7.0 g. (87% yield). An analytical sample recrystallized from hexane has a melting point of 172°-173° C.

IR: C=N, 1705 cm⁻¹ (CCl₄).

NMR: (CDCl₃, δ) 5.88 (1H, d, J = 5.5 Hz, C-1'), 4.50 (1H, d of d, J = 5.5 Hz, C-2'), 4.37 (1H, m, C-3), 4.3 (2H, broad, NH₂), 3.83 (1H, m, C-4), 3.62 (2H, m, C-5), 0.90 (18H, s, t-butyl), 0.13 and 0.08 (9H, s, CH₃).

Elemental Analysis: Calcd.: C, 53.69; H, 9.51; N, 6.96. Found: C, 53.24; H, 9.38; N, 6.78.

TLC: Rf = 0.22 (85% EtOAc/Hexane)

Glpc: Ret. time = 1.9 min. (270°, 6'-3.8% UCW - 98)

GC-MS: no M⁺ at 402, 387 (2%, M-CH₃), 345 (12%, M-t-butyl), 261 (29%), 97 (35%), 89 (100%).

EXAMPLE II

3',5'-bis(o-tert-butyldimethylsilyl)-β-D-arabinofuran[1',2':4,5]-oxazolo-1,3,5-triazin-5-N-methyl-4,6-dione

Part A

To 51 mg. (1 mmole) of 45% NaH (washed twice with hexane to remove oil) in 7 ml. dry THF (distilled prior to use from Na-benzophenone) under N₂ at room temperature is added 402 mg. (1 mmole) of 2-amino-3',5'-bis(o-tert-butyldimethylsilyl)-β-D-arabinofuran-[1',2':4,5]-2-oxazoline in several portions. After 30 minutes stirring 75 µl. (1.25 mmole) of methylisocyanate is added dropwise over 5-10 minutes. After stirring for 1 hour the solution is either worked up or 200 mg. (1.2 mmole) of 1,1'-carbonyl diimidazol is added and stirred for another 2 hours. If the intermediate is desired the work-up procedure described in Example II (Part B) yields 445 mg. (97% yield) of a white solid which appears by TLC and NMR to be one isomer.

Analysis:

IR: NH, 3350 and 3500 cm⁻¹ (CHCl₃) C=O 1660 cm⁻¹, Amide II band 1520 cm⁻¹.

NMR: (CDCl₃, δ) 6.4 (1H, broad, NH), 5.95 (1H, d, J = 5.5 Hz, C-1'), 4.78 (1H, d, J = 5.5 Hz, C-2'), 2.85 (3H, d, J = 5 Hz, N—CH₃).

Part B

If the reaction is continued by addition of the 1,1'-carbonyl diimidazol the work-up includes taking the heterogeneous solution up in 100 ml. ethyl acetate and 50 ml. of water, washing the organic layer with 50 ml. of brine. The aqueous solution is back-extracted with ethyl acetate which is then combined with the original organic phase after washing with brine and drying over Na₂SO₄. Concentration under reduced pressure yields an oil which is chromatographed on 150 g. of silica gel with 40% ethyl acetate/hexane to afford ultimately 414 mg. (85% yield) of 3',5'-bis(o-tert-butyldimethylsilyl)-β-D-arabinofuran[1',2':4,5]-oxazolo-1,3,5-triazin-5-N-methyl-4,6-dione.

IR: C=O, C=N at 1760, 1700, 1660 cm⁻¹. (CCl₄)

NMR: (CDCl₃, δ) 6.41 (1H, d, J = 5.5 Hz, C-1'), 5.18 (1H, d of d, J = 5.5 Hz, C-2'), 3.32 (3H, 5, N—CH₃), 0.90 and 0.83 (18H, s, t-butyl).

UV: (EtOH) λ$_{max}$ = 217 (ε = 5250); λ$_{max}$ = 275 (ε = 250).

TLC: Rf = 0.63 final product (50% EtOAc/hexane); Rf = 0.48 intermediate

Glpc: Ret. time = 8.9 min., 6'-3.8% UCW - 98, 270° (final product; intermediate decomposes to starting material in gc).

GC-MS: M 485 (<1%), 470 (3%, M' - methyl), 428 (62%, M' - t-butyl), 282 (13%), 261 (29%), 189 (100%).

EXAMPLE III

3',5'-bis(O-acetyl)-β-D-arabinofuran[1',2':4,5]-oxazolo-1,3,5-triazin-5-N-methyl-4,6-dione.

To 2.5 g. (5.15 L mmole) of 3',5'-bis(o-tert-butyldimethylsilyl)-β-D-arabinofuran[1',2':4,5]-oxazolo-1,3,5-triazin-5-N-methyl-4,6-dione in 50 ml. of dry THF under $N_2$ at room temperature with stirring is added 15.5 ml. of a 1M tetra-n-butylammonium fluoride solution (prepared by the procedure of J. Pless, J. Org. Chem., 39, 2645 (1974)). After two hours the solution is concentrated in vacuo and the resultant gum taken up in 20 ml. of pyridine to which is added 5 ml. of acetic anhydride and stirred under $N_2$ at room temperature for four hours. Upon concentrating the solution is applied to a 150 g. silica gel column prepared in ethyl acetate and after an initial 200 ml. elution, the solvent is changed to 5% methanol/ethyl acetate, 1.2 g. (70%) of the product 3',5'-bis(O-acetyl)-β-D-arabinofuran[1',2':4,5]-oxazolo-1,3,5-triazin-5-N-methyl-4,6-dione as named according to Chemical Abstract nomenclature as 2H-furo[2',3':4,5]-oxazolo[3,2-a]-1,3,5-triazine-2,4-(3H)-dione, 5a,7,8,8a-tetrahydro-8-hydroxy-7-(hydroxymethyl)-3-methyl-, diacetate, [5aR-(5aα, 7β, 8a, 8aα)] is recovered as a white solid after trituration with ether.

NMR (DMSO-$d_6$) 6.38 (1H, d, J = 5.5 Hz, C-1'), 5.55 (1H, d, J = 5.5 Hz, C-2'), 5.33 (1H, m, C-3'), 4.53 (1H, m, C-4'), 4.1 (2H, m, C-5'), 3.15 (3H, s, N—$CH_3$), 2.11 and 1.95 (6H, s, $CH_3CO$).

Tlc Rf = 0.57 (5% MeOH/EtOAc)
Glpc. Ret. time = 4.8 min (240°, 4'-3.8% UCW-98)
GC-MS $M^+$ = 341 (10%), 298 (3%, $M^+$-$CH_3CO$), 239 (12%, m+-$CH_3$-2$CH_3$CO-H), 151 (75%), 43 (100%).

EXAMPLE IV

β-D-arabinofuran[1',2':4,5]-oxazolo-1,3,5-triazin-5-N-methyl-4,6-dione

To 50 mg. (0.15 mmol) of 3',5'-bis-(o-acetyl)-β-D-arabinofuran[1',2':4,5]-oxazolo-1,3,5-triazin-5-N-methyl-4,6-dione is added under nitrogen at room temperature with stirring 2 ml. of ammonia saturated methanol. After 30 minutes the solution is concentrated under reduced pressure and the residue washed twice with chloroform (to remove acetamide), taken up in water and lyophilized to yield 35 mg. of β-D-arabinofuran[1',2':4,5]-oxazolo-1,3,5-triazin-5-N-methyl-4,6-dione as a white solid (93%, quite hygroscopic).

NMR ($D_2O$) 6.58 (1H, d, J = 5 Hz, C-1'), 5.43 (1H, d, J = 6 Hz, C-2'), 4.5 (1H, m, C-3'), 4.4 (1H, m, C-4'), 3.65 (2H, m, C-5'), 3.19 (3H, s, $NCH_3$).

Tlc Rf = 0.46 (30% MeOH/EtOAc)

EXAMPLE V

β-D-arabinofuranosyl-1,3,5-triazine-5-N-methyl-2,4,6-trione

To 25 mg. (0.1 mmol) of β-D-arabinofuran[1',2':3,5]-oxazolo-1,3,5-triazin-5-N-methyl-4,6-dione is added 2 ml. of 0.1M potassium hydroxide. After stirring at room temperature for fifteen minutes the solution is rapidly neutralized with Amberlite IR 120 (H+) resin, filtered, and lyophilized.

NMR ($D_2O$) essentially identical to starting material except for slight upfield shift for C-2' and N—$CH_3$ (0.04 and 0.02).

Tlc Rf = 0.59 (30% MeOH/EtOAc)
(note: tlc and nmr indicated some base cleavage).

β-D-arabinofuranosyl-1,3,5-triazine-5-N-methyl-2,4,6-trione can also be obtained from 2',3',5'-tri-O-acetyl-β-D-arabinofuranosyl-1,3,5-triazine-5-N-methyl-2,4,6-trione by treatment with ammonia saturated methanol according to the procedure of Example 4.

EXAMPLE VI

β-D-arabinofuran[1',2':4,5]-oxazolo-1,3,5-triazin-5-N-methyl-4,6-dione

To 22.26 g. (70 mmole) of 3',5'-bis(O-tri-methylsilyl)-β-D-arabinofuran[1',2':4,5]-oxazolo-1,3,5-triazin-5-N-methyl-4,6-dione, 300 ml. of dry THF at −78° C. under $N_2$ is added 47 ml. of n-butyl lithium (approximately 1.6 M in hexane). After the addition is complete (15 minutes) the cold bath is removed and 5.25 ml. of methyl isocyanate is added at a reaction temperature of 0° C. After 5 min. 12.5 g. (77 mmole) of 1,1'-carbonyl diimidazole is added and the reaction stirred for one hour while warming to room temperature. The solution is taken up in ethyl acetate/$H_2O$ (2 L: 1L), shaken, and separated. The aqueous phase is re-washed with 1 L of ethyl acetate; the organic phases are combined, dried over sodium sulfate, and concentrated in vacuo. To the residue is added 300 ml. of methanol, 30 ml. of water, and 5 ml. of acetic acid. The resulting solution is concentrated at reduced pressure at less than 40° C. followed by azeotroping under the same conditions with 600 ml. of methanol followed by 600 ml. of acetonitrile. The resulting gum is chromatographed on 400 g. of silica gel with 5% methanol/ethyl acetate to 10% to yield 5.93 g. of a white solid (33% yield). Recrystallization from 25% methanol/ethyl acetate gives m.p. 246°-8°. Alternatively, the product can be isolated by trituration of the crude with 20% methanol/ethyl acetate followed by filtration. The solid is washed once with the same solvent to remove the last traces of imidazole.

NMR ($D_2O$): 6.59 (1H, d, J = 5.5 Hz, 1'), 5.50 (1H, d, J = 5.5 Hz, 2'), 4.7-4.3 (2H, m, 3',4'), 3.64 (2H, d, J = 3.5 Hz, 5'), 3.23 (3H, s, N—$CH_3$).

Analysis Calc'd. for $C_9H_{11}N_3O_6$: C, 42.03; H, 4.31; N, 16.34. Found: C, 41.93; H, 4.37; N, 16.14.

The compouns of the present invention are presented for administration to humans in unit dosage forms, such as tablets, capsules, pills, powders, granules, sterile parenteral solutions or suspensions, oral solutions or suspensions, and oil-in-water and water-in-oil emulsions containing suitable quantities of compounds of formula I or II.

For oral administration, either solid or fluid unit dosage forms can be prepared. For preparing solid compositions such as tablets, the compound of formula I is mixed with conventional ingredients such as talc, magnesium stearate, dicalcium phosphate, magnesium aluminum silicate, calcium sulfate, starch, lactose, acacia, methylcellulose, and functionally similar materials as pharmaceutical diluents or carriers. Capsules are prepared by mixing the compound with an inert pharmaceutical diluent and filling the mixture into a hard gelatin capsule of appropriate size. Soft gelatin capsules are prepared by machine encapsulation of a slurry of the compound with an acceptable vegetable oil, light liquid petrolatum or other inert oil.

Fluid unit dosage forms for oral administration such as syrups, elixirs, and suspensions can be prepared. The water-soluble forms can be dissolved in an aqueous vehicle together with sugar, aromatic flavoring agents and preservatives to form a syrup. An elixir is prepared by using a hydroalcoholic (ethanol) vehicle with suitable sweeteners such as sugar and saccharin, together with an aromatic flavoring agent.

Suspensions can be prepared with an aqueous vehicle with the aid of a suspending agent such as acacia, tragacanth, methylcellulose and the like.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilized before filling into a suitable vial or ampul and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compound is suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the compound.

Parenteral solutions can be administered intravenously as well as by other parenteral routes of administration, e.g., intraperitoneally, subcutaneously and intramuscularlly. Parenteral suspensions are unsuited for intravenous administration.

Additionally, a rectal suppository can be employed to deliver the active compound. This dosage form is of particular interest where the mammal cannot be treated conveniently by means of other dosage forms, such as orally or parenterally as in the case of young children or debilitated persons. The active compound can be incorporated into any of the known suppository bases by methods known in the art. Examples of such bases include the cocoa butter, polyethylene glycols (Carbowaxes), polyethylene sorbitan monostearate, and mixtures of these with other compatible materials to modify the melting point or dissolution rate. These rectal suppositories can weigh from about 1 to 2.5 gm.

EXAMPLE VII

A sterile aqueous dispersion suitable for intramuscular use, and containing 250 mg. of β-D-arabinofuran[1',2':4,5]-oxazolo-1,3,5-triazin-5-N-methyl-4,6-dione in each ml., is prepared from the following ingredients:

| | |
|---|---|
| β-D-arabinofuran[1',2':4,5]-oxazolo-1,3,5-triazin-5-N-methyl-4,6-dione, sterile micronized | 250 gm. |
| Water for injection, q.s. | 1000 ml. |

In a sterile container add 500 ml. of the Water for Injection and commence stirring. Slowly add the sterilized micronized compound. After all the compound is wetted and mixed, q.s. to volume. Continue stirring for 60 min. Aseptically fill the dispersion into sterile vials and seal the vials.

The aqueous dispersion so prepared is administered at five sites to an adult human at a dose of 1 ml. per injection site every eight hours 3 to 7 days prior to antigenic insult and continued for not less than 15 days after insult for alleviation of the rejection response following organ transplants, including skin grafts.

EXAMPLE VIII

Tablets for Oral Administration

1000 Scored tablets for oral use, each containing 500 mg. of β-D-arabinofuran[1',2':4,5]-oxazolo-1,3,5-triazin-5-N-methyl-4,6-dione are prepared from the following types and amounts of ingredients:

| | | |
|---|---|---|
| β-D-arabinofuran[1',2':4,5]-oxazolo-1,3,5-triazin-5-N-methyl-4,6-dione | 500 | gm. |
| Starch, U.S.P. | 35 | gm. |
| Talc, U.S.P. | 25 | gm. |
| Calcium stearate | 3.5 | gm. |

The powdered β-D-arabinofuran[1',2':4,5]-oxazolo-1,3,5-triazin-5-N-methyl-4,6-dione is granulated with a 4% w./v. aqueous solution of methylcellulose U.S.P. To the dried granules is added a mixture of the remainder of the ingredients and the final mixture is compressed into tablets of proper weight.

The foregoing composition is administered to an adult human at a dose of two to four tablets four times a day 3 to 7 days prior to antigentic insult and continued for not less than 15 days after insult for alleviation of the rejection response following organ transplants, including skin grafts.

EXAMPLE IX

Following the procedure of Examples VII and VIII pharmaceutical compositions are prepared substituting equimolar amounts of a compound characterized by having the formula:

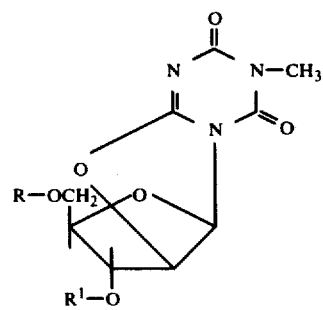

where R and $R^1$ can be the same or different, and are selected from the group consisting of hydrogen; adamantoyl, substituted with zero through one substituent selected from the group consisting of —$CH_2CO_2H$ and —$CH_2CO_2CH_3$; or the radical

wherein X is selected from the group consisting of phenyl, substituted with zero through three substituents, which can be the same or different and are selected from the group consisting of halogen, alkyl of one through six carbon atoms, dialkylamino where the alkyl groups contain one through six carbon atoms and can be the same or different, trifluoromethyl, alkoxy where the alkyl group contains one through six carbon atoms, cyano, carboxy, carbomethoxy, and carbethoxy; α- or β-naphthyl; alkyl of one through 12 carbon atoms, substituted with zero through one substituents selected from the group consisting of phenyl, cyano, nitro, halogen and carboxy; and alkoxy where the alkyl group contains one through 12 carbon atoms, substituted with zero through one substituents selected from the group consisting of phenyl, cyano, nitro, halogen and carboxy; provided that when one member is not hydrogen, the other member is the same or hydrogen; for β-D-arabinofuran[1',2':4,5]-oxazolo-1,3,5-triazin-5-N-methyl-4,6-dione to provide similar therapeutic properties.

EXAMPLE X

Following the procedure of Examples VII and VIII pharmaceutical compositions are prepared substituting equimolar amounts of a compound characterized by having the formula:

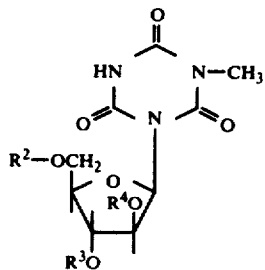

II wherein $R^2$, $R^3$ and $R^4$ can be the same or different; and are selected from the group consisting of hydrogen; adamantoyl, substituted with zero through one substituents selected from the group consisting of $CH_2CO_2H$ and $CH_2CO_2CH_3$; of the radical

wherein X is selected from the group consisting of phenyl, substituted with zero through three substituents, which may be the same or different and are selected from the group consisting of halogen, alkyl of one through six carbon atoms, dialkylamino where the alkyl groups contain one through six carbon atoms and may be the same or different, trifluoromethyl, alkoxy where the alkyl group contains one through six carbon atoms, cyano, carboxy, carbomethoxy and carbethoxy; α- or β-naphthyl; alkyl of one through 12 carbon atoms, substituted with zero through one substituents selected from the group consisting of phenyl, cyano, nitro, halogen and carboxy; and alkoxy where the alkyl group contains one through 12 carbon atoms, substituted with zero through one substituents selected from the group consisting of phenyl, cyano, nitro, halogen, and carboxy; provided that two or more of the members ($R^2$, $R^3$ and $R^4$) are the same and when a first member is not hydrogen, the other members are the same as the first member or hydrogen and further provided that when $R^3$ is hydrogen, one of $R^2$ and $R^4$ must also be hydrogen and still further provided that when $R^3$ is not hydrogen, $R^2$ and $R^4$ cannot both be hydrogen; for β-D-arabinofuran[1',2':4,5]-oxazolo-1,3,5-triazin-5-N-methyl-4,6-dione to provide similar therapeutic properties.

EXAMPLE XI

Following the procedure of Examples VII and VIII pharmaceutical compositions are prepared substituting equimolar amounts of each of the compounds of Tables I and II for β-D-arabinofuran[1',2':4,5]-oxazolo-1,3,5-triazin-5-N-methyl-4,6-dione to provide similar therapeutic properties.

EXAMPLE XII

A sterile aqueous solution for parenteral use, containing 100 mg. per ml. of β-D-arabinofuran[1',2':4,5]-oxazolo-1,3,5-triazin-5-N-methyl-4,6-dione is prepared from the following ingredients:

| | |
|---|---|
| β-D-arabinofuran[1',2':4,5]-oxazolo-1,3,5-triazin-5-N-methyl-4,6-dione | 100 gm. |
| Water for injection, q.s. | 1000 ml. | the compound is dissolved in sufficient water to make 1000 ml. and sterile filtered.

The foregoing composition is administered to an adult human by intravenous drip so as to provide a daily dose of 100 mg./kg./day. The dose is administered 3 to 7 days prior to antigenic insult and continued for not less than 15 days after insult for alleviation of the rejection response following organ transplants, including skin grafts.

EXAMPLE XIII

Following the procedure of Example XII, sterile aqueous solutions are prepared substituting equimolar amounts of 3',5'-bis(O-acetyl)-β-D-arabinofuran[1',2':4,5]-oxazolo-1,3,5-triazin-5-N-methyl-4,6-dione; β-D-arabinofuranosyl-1,3,5-triazine-5-N-methyl-2,4,6-trione; and 2',3',5'-tri-O-acetyl-β-D-arabinofuranosyl-1,3,5-triazine-5-N-methyl-2,4,6-trione for β-D-arabinofuran[1',2':4,5]-oxazolo-1,3,5-triazin-5-N-methyl-4,6-dione of Example XII to provide similar therapeutic properties.

I claim:

1. A compound of the formula:

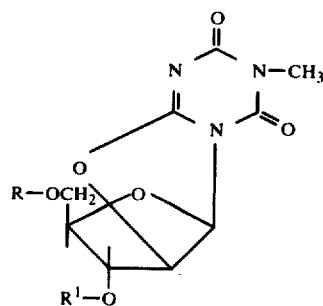

I where R and R¹ can be the same or different, and are selected from the group consisting of hydrogen; adamantoyl; adamantoyl substituted with one substituent selected from the group consisting of —CH₂CO₂H and —CH₂CO₂CH₃; or the radical

wherein X is selected from the group consisting of phenyl, phenyl substituted with one through three substituents, which can be the same or different and are selected from the group consisting of halogen, alkyl of one through six carbon atoms, dialkylamino where the alkyl groups contain one through six carbon atoms and can be the same or different, trifluoromethyl, alkoxy where the alkyl group contains one through six carbon atoms, cyano, carboxy, carbomethoxy, and carbethoxy; α- or β-naphthyl; alkyl of one through 12 carbon atoms; alkyl of one through 12 carbon atoms substituted with one substituent selected from the group consisting of phenyl, cyano, nitro, halogen and carboxy; alkoxy where the alkyl group contains one through 12 carbon atoms; and alkoxy where the alkyl group contains one through 12 carbon atoms, substituted with one substituent selected from the group consisting of phenyl, cyano, nitro, halogen and carboxy; provided that when one member is not hydrogen, the other member is the same or hydrogen.

2. A compound according to claim 1 wherein R¹ is hydrogen.

3. A compound according to claim 1 wherein R is hydrogen.

4. A compound according to claim 1 wherein R¹ is hydrogen and R is the radical

wherein X is selected from the group consisting of lower alkyl of one through four carbon atoms, phenyl and 2-carboxyethyl.

5. A compound according to claim 1 wherein R¹ is hydrogen and R is the radical

wherein X is phenyl, phenyl substituted with one through three substituents, which can be the same or different and are selected from the group consisting of halogen; adamantoyl; adamantoyl substituted with one substituent selected from the group consisting of CH₂CO₂H and CH₂CO₂CH₃ or the radical

wherein X is selected from the group consisting of phenyl, phenyl substituted with one through three substituents, which can be the same or different and are selected from the group consisting of halogen, alkyl of one through six carbon atoms, dialkylamino where the alkyl groups contain one through six carbon atoms and can be the same or different, trifluoromethyl, alkoxy where the alkyl group contains one through six carbon atoms, cyano, carboxy, carbomethoxy and carbethoxy; α- or β-naphthyl; alkyl of one through 12 carbon atoms; alkyl of one through 12 carbon atoms substituted with one substituent selected from the group consisting of phenyl, cyano, nitro, halogen and carboxy; alkoxy where the alkyl group contains one through 12 carbon atoms; and alkoxy where the alkyl group containing one through 12 carbon atoms substituted with one substituent selected from the group consisting of phenyl, cyano, nitro, halogen and carboxy.

6. A compound according to claim 1 wherein R¹ is hydrogen and R is the radical

wherein X is alkoxy where the alkyl group contains one through six carbon atoms.

7. 3',5'-bis(O-acetyl)-β-D-arabinofuran[1',2':4,5]-oxazolo-1,3,5-triazin-5-N-methyl-4,6-dione, a compound according to claim 1.

8. β-D-arabinofuran[1',2':4,5]-oxazolo-1,3,5-triazin-5-N-methyl-4,6-dione, a compound according to claim 1.

9. A process for the production of 3',5'-bis(O-tert-butyldimethylsilyl)-β-D-arabinofuran[1',2':4,5]-oxazolo-1,3,5-triazin-5-N-methyl-4,6-dione, which comprises:
 1. silylating 2-amino-β-D-arabinofuran[1',2':4,5]-2-oxazoline with tert-butyldimethylsilyl chloride;
 2. ionizing the 2-amino-3,5-bis(O-tert-butyldimethylsilyl)-β-D-arabinofuran[1',2':4,5]-2-oxazoline with a base selected from the group consisting of n-butyl lithium, potassium t-butoxide or sodium hydride in an aprotic, polar solvent in an inert atmosphere followed by addition of methyl isocyanate; and
 3. closing the ring of the N-methylcarbamate.

10. The process according to claim 9, wherein the base is sodium hydride.

11. The process according to claim 10, wherein the ring-closure is effected with 1,1'-carbonyl diimidazole.

12. A process for the production of β-D-arabinofuran[1',2':4,5]-oxazolo-1,3,5-triazin-5-N-methyl-4,6-dione, which comprises:
 1. silylating 2-amino-β-D-arabinofuran[1',2':4,5]-2-oxazoline with tert-butyldimethylsilyl chloride;
 2. ionizing the 2-amino-3,5-bis(O-tert-butyldimethylsilyl)-β-D-arabinofuran[1',2':4,5]-2-oxazoline with a base selected from the group consisting of n-butyl lithium, potassium t-butoxide or sodium hydride in an aprotic, polar solvent in an inert atmosphere followed by addition of methyl isocyanate;
 3. closing the ring of the N-methylcarbamate; and
 4. removing the tert-butyldimethylsilyl protecting groups from the 3',5'-bis(O-tert-butyldimethylsilyl)-β-D-arabinofuran[1',2':4,5]-oxazolo-1,3,5-triazin-5-N-methyl-4,6-dione.

13. The process according to claim 12, wherein the base is sodium hydride, the ring closure is effected with 1,1'-carbonyl diimidazole and the tert-butyldimethylsilyl protecting groups are removed with tetra-n-butyl ammonium fluoride.

14. A process for the production of β-D-arabinofuran[1',2':4,5]-oxazolo-1,3,5-triazin-5-N-methyl-4,6-dione, which comprises:
 1. ionization of 3',5'-bis(O-trimethylsilyl)-β-D-arabinofuran[1',2':4,5]-oxazolo-1,3,5-triazin-5-N-methyl-4,6-dione with a suitable base in a solvent selected from the group consisting of THF, dimethoxyethane, dioxane or diglyme, followed by addition of methyl isocyanate;

2. closing the ring of the N-methylcarbamate; and 3. removing the tri-methylsilyl protecting groups with mild aqueous acid hydrolysis.

15. The process according to claim 14, wherein the base is n-butyllithium.

16. The process according to claim 15, wherein the ring closure is effected with 1,1'-carbonyl diimidazole.

* * * * *